United States Patent [19]

Miley et al.

[11] Patent Number: 4,985,546
[45] Date of Patent: Jan. 15, 1991

[54] POLYOXYLALKYLENE AMINO DIOL SUBSTITUTED COLORANTS

[75] Inventors: John W. Miley, Campobello; John W. Rekers, Spartanburg, both of S.C.

[73] Assignee: Milliken Research Corporation, Spartanburg, S.C.

[21] Appl. No.: 371,907

[22] Filed: Jun. 19, 1989

Related U.S. Application Data

[62] Division of Ser. No. 135,421, Dec. 21, 1987.

[51] Int. Cl.$^5$ .................. C09B 1/14; C09B 23/00; C09B 29/00; C09B 56/16
[52] U.S. Cl. .................. 534/729; 534/573; 546/297; 548/375; 549/353; 549/373; 549/374; 549/451; 552/289; 564/505; 564/443; 564/475
[58] Field of Search .................. 534/729, 573 P; 549/353, 451, 373, 374; 564/505, 475, 443; 548/375; 546/297; 552/289

[56] References Cited

U.S. PATENT DOCUMENTS

| | | | |
|---|---|---|---|
| 801,484 | 10/1905 | Stephan et al. | 549/13 X |
| 2,428,805 | 10/1947 | Kharasch | 260/338 |
| 2,445,393 | 7/1948 | Fourneau | 260/338 |
| 2,606,907 | 8/1951 | Blicke | 549/373 X |
| 2,606,908 | 8/1952 | Blicke | 260/338 |
| 2,699,452 | 1/1955 | Wilkes et al. | 564/505 X |
| 2,995,553 | 8/1961 | Sommers | 564/505 X |
| 3,154,534 | 10/1964 | Gale et al. | 534/724 |
| 3,154,535 | 10/1964 | Graham et al. | 534/724 |
| 3,179,697 | 4/1965 | Frump | 260/570.6 |
| 3,337,525 | 8/1967 | Peters et al. | 564/729 |
| 3,352,916 | 11/1967 | Zech | 564/475 X |
| 3,580,952 | 5/1971 | Moschel | 260/584 |
| 3,888,882 | 6/1975 | Richter et al. | 549/373 X |
| 4,031,112 | 6/1977 | Oppenlaender et al. | 549/373 X |
| 4,113,721 | 9/1978 | Hauser et al. | 534/729 |
| 4,294,764 | 10/1981 | Rinehart | 549/373 X |
| 4,351,934 | 9/1982 | Kluger et al. | 528/111 |
| 4,465,869 | 8/1984 | Takaishi et al. | 568/672 |
| 4,526,994 | 7/1985 | Niedballa et al. | 549/729 |
| 4,537,980 | 8/1985 | Greenshields | 549/374 X |
| 4,570,007 | 2/1986 | Niedballa et al. | 549/451 |
| 4,601,725 | 7/1986 | Keller et al. | 534/729 X |
| 4,618,717 | 10/1986 | Benxen et al. | 564/475 |
| 4,636,568 | 1/1987 | Simon et al. | 549/13 |
| 4,726,844 | 2/1988 | Greenwood | 534/729 X |

FOREIGN PATENT DOCUMENTS 0072621 2/1983 European Pat. Off. ............ 534/729

Primary Examiner—Floyd D. Higel
Attorney, Agent, or Firm—Timothy J. Monahan; H. William Petry

[57] ABSTRACT

A substituted colorant which may be copolymerized with a condensation polymer to provide a covalently bound, nonextractable coloring, having the formula

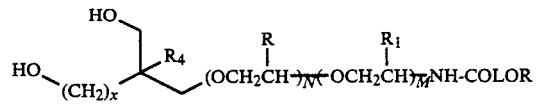

wherein R and $R_1$ are independently selected from hydrogen or lower alkyl; $R_4$ is selected from hydrogen or lower alkyl; x is 0 or 1; N and M are each integers of from 1 to about 100 and the sum of N and M is from 3 to about 100. The hydroxyl groups are protected by formation of a ring structure during alkoxylation and amination of the substituent.

3 Claims, No Drawings

POLYOXYLALKYLENE AMINO DIOL SUBSTITUTED COLORANTS

This is a division of co-pending application Ser. No. 07/135,421, filed Dec. 21, 1987.

The present invention relates to polyoxyalkylene amino 1,3-dioxanes and 1,3-dioxolanes and to alcohols derived therefrom. The present invention also relates to a process for preparing primary amino polyoxyalkylene 1,3-dioxanes and 1,3-dioxolanes and to alcohols derived therefrom. The compounds of the present invention are useful as intermediates in the preparation of polyalkyleneoxy-substituted colorants, e.g. colorants that may be reacted with condensation polymers to become covalently bonded to such polymers. Many other uses for such compounds will be apparent to those skilled in the art. For instance, the compounds may be useful modifiers for polyurethanes, epoxy modifiers, cross-linking agents for, e.g., polyesters, especially for coating end use applications, etc.

The polyoxyalkylene amino compounds of the present invention may be described as follows:

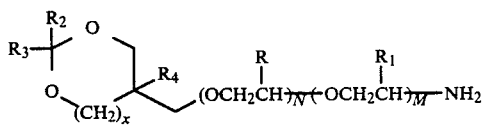
I.

wherein R and $R_1$ are independently selected from hydrogen or a lower alkyl group, $R_2$ and $R_3$ are independently selected from hydrogen, phenyl, or lower alkyl groups, $R_4$ is selected from hydrogen or a lower alkyl group; x is 0 or 1; N and M are each integers of from 1 to about 100 and the sum of N and M is from 2 to about 100; also disclosed are polyoxyalkylene amino alcohol compounds which may be derived from the compounds of formula I above having the formula:

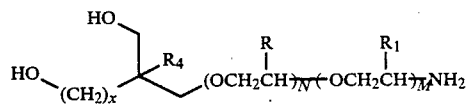
II.

wherein R, $_1$,$R_4$, x, N and M have the values given above.

As used herein the phrase lower alkyl groups refers to alkyl groups having from one to about three carbon atoms. It is also to be understood that the designation:

represents either homopolymers, block copolymers or random copolymers.

It is known that primary amino compounds may be obtained by amination (catalytic or otherwise) of free reactive hydroxyl groups. If, however, compounds are desired which contain within the same molecule free reactive hydroxyl groups and at least one free primary amino group, these compounds may not be obtainable by available synthesis routes.

Thus, according to an embodiment of the present invention a method is least two reactive hydroxyl groups or a latent hydroxyl precursor functionality.

The compounds of the present invention may be prepared using polyol starting materials containing at least three hydroxyl groups, two of which are protectable by a cyclic 1,3-dioxane or dioxolane functionality, by reacting those hydroxyl groups with a suitable ketone or aldehyde. Examples of such polyols include glycerol, trimethylol propane, trimethylol ethane, sorbitol and mannitol among others. Glycerol is preferred. Examples of suitable ketones or aldehydes include acetone, 2-butanone, cyclohexanone, acetophenone, benzophenone and benzaldehyde, among others. Acetone and cyclohexanone are preferred.

The first step in the synthesis of the compounds of the present invention is to protect the hydroxy groups as desired by reacting the polyol with the ketone or aldehyde under suitable reaction conditions, usually at a temperature of from about 40° to about 175° C. in the presence of an acid catalyst to form the corresponding ketal or acetal by a condensation reaction to eliminate water.

The resulting compounds containing at least one free hydroxyl group are suitable for the alkoxylation reaction, normally conducted under basic conditions, which involves reaction with a suitable epoxide such as ethylene oxide, propylene oxide, butylene oxide or mixtures thereof. Typically from about 1 to about 100 moles, preferably from 1 to about 40 moles of epoxide per mole of ketal of acetal may be employed. Conventional reaction conditions may be employed, e.g., temperatures of from about 80° C. to about 150° C. and modestly elevated pressures. Suitable catalysts include tertiary amines, sodium hydroxide, potassium hydroxide and the corresponding hydrides and alkoxides. The resultant polyoxyalkylene ketal or acetal alcohol reaction products may be characterized by the formulas:

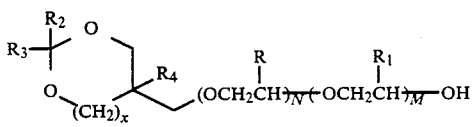

The thus prepared polyoxyalkylene 1,2-dioxane and 1,3-dioxolane intermediates may then be reductively aminated in the presence of hydrogen and ammonia using a nickel-copper-chromia catalyst of the type disclosed by Meakey, U.S. Pat. No. 3,654,370. Such catalyst may be prepared by the reduction of a mixture of the oxides of nickel, copper and chromium in the presence of hydrogen at a temperature of about 250° C. to 400° C. Calculated on a oxide-free basis, the catalyst contains about 60–85 mole percent nickel, 14–37 mole percent copper and 1–5 mole percent chromium. A particularly preferred catalyst composition is one containing 70–80 mole percent nickel, 20–25 mole percent copper and 1–5 mole percent chromium.

The process is conducted at a temperature within the range of from about 150° to 275° C. with a preferred range being from 200° to 250° C. The pressure may be varied from 500–5000 PSIG with the preferred range being 2000–4000 PSIG. The process may be conducted with or without a solvent Solvents that may be employed include water and inert hydrocarbons such as heptane and cyclohexane or nonreactive alcohols such as tertiary butyl alcohol A preferred solvent is liquid ammonia which can be present in a 10–40 mole excess with a 20–30 mole excess being preferred. It is convenient to use ammonia as a solvent since ammonia is necessary to the reaction.

The process may be conducted batch-wise, using, for instance, Raney nickel catalyst, or it may be conducted continuously. Continuous operation is preferred, since, in general, batch processes are slow and require filtration to remove the catalyst.

According to an alternative embodiment, the amination may be effected by first oxidizing the alcohol to the corresponding carbonyl compound, and then reductively aminating the carbonyl compound using conventional methodology.

The resultant reductive amination product will be comprised primarily of a polyoxyalkylene amino compound as set forth in formula I above.

The corresponding amino alcohol compounds represented by formula II above may be easily derived from the compounds of formula I by acid catalyzed hydrolysis of the 1,3-dioxane or 1,3-dioxolane protective functions.

As mentioned above the polyoxyalkylene amino 1,3-dioxanes and 1,3-dioxolanes of the present invention and the alcohols derived therefrom have been found to be quite useful in the manufacture of polymer bound colorants. Such colorants may be represented by the following structural formula:

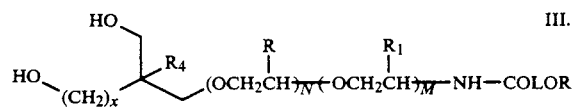

where the values R, $R_1$, $R_4$, x, N and M all have the values given above and the designation "COLOR" represents any of a wide variety of chromophoric moieties including, but not limited to, nitroaryl, methines, azos, disazos, anthraquinones, pyrazolones and pyridones. Preferred chromophoric molecules include methines, anthraquinones, pyrazolones, pyridones and nitroaryls.

The compounds of formula III above may be prepared by alternative paths A and B which are depicted in Scheme I below:

large amount of acid must be neutralized producing a large amount of salt which must be disposed of. The invention may be further understood by reference to the following examples which are not to be construed as limiting the scope of the invention as defined in the claims. Unless otherwise indicated all parts and percentages are by weight.

EXAMPLES 1–4

Isopropylidene glycerol (solketal) was alkoxylated using 1% by weight of potassium hydroxide catalyst. The reactions were run at 250° F. until the stoichiometric amount of ethylene oxide and/or propylene oxide had reacted to provide the alkoxylates listed in Table 1.

TABLE I

| EXAMPLE | MOLES ALKYLENE OXIDE | | HYDROXYL NUMBER (Mg KOH/g) | |
|---|---|---|---|---|
| | ETHYLENE | PROPYLENE | Theory | Found |
| 1 | 0 | 3 | 183 | 177 |
| 2 | 0 | 4 | 154 | 157 |
| 3 | 1 | 3 | 160 | 163 |
| 4 | 4 | 4 | 104 | 109 |

EXAMPLES 5–8

These examples illustrate the reductive amination of the alkoxylates of isopropylidene gylcerol of Examples 1–4 to produce a ketal polyoxyalkylene amines of this invention. The ketal polyoxyalkylene alcohol of Example 1 was reductively aminated under pressure with hydrogen and ammonia in a continuous reactor over a nickel catalyst. The alcohols of examples 2–4 were similarly converted to the corresponding amines as shown in Table 2.

TABLE 2

| EXAMPLE | TOTAL ACETYLATABLES MEq/g | TOTAL AMINE MEq/g | PRIMARY AMINE | |
|---|---|---|---|---|
| | | | MEq/g | THEORY |
| 5 | 3.33 | 3.06 | 3.04 | 3.15 |
| 6 | 2.92 | 2.89 | 2.85 | 2.90 |
| 7 | 2.87 | 2.67 | 2.65 | 2.91 |
| 8 | 2.05 | 2.03 | 2.05 | 1.94 |

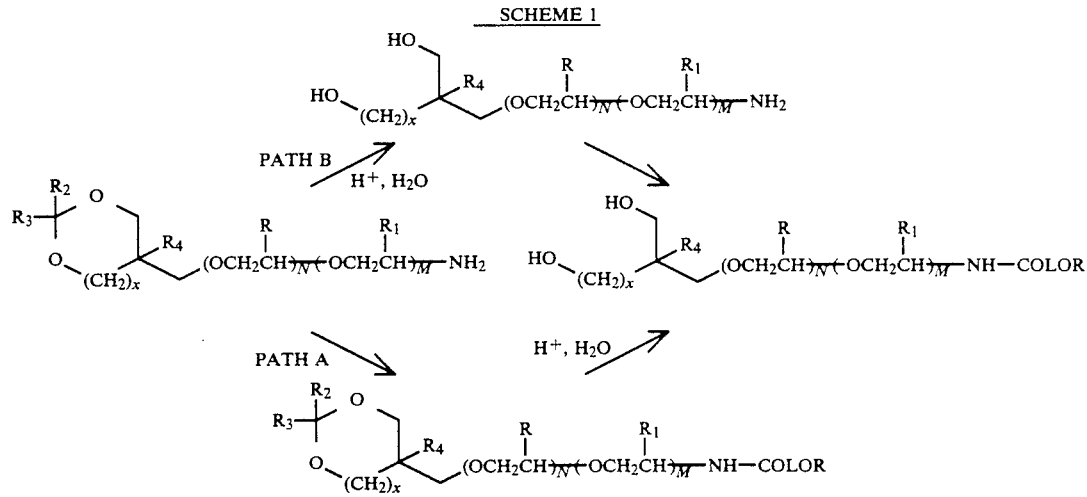

SCHEME 1 path A is the preferred path because path B requires that all of the free amine be first neutralized before acid catalyst is available to cleave the 1,3-dioxanes or 1,3-dioxolanes. Then once the functionality is removed a

EXAMPLE 9

This example demonstrates the synthesis of anthraquinone colorants from the polyoxyalkylene amino ketals. A stirred mixture of 4.84 g (0.0200 moles) of leucoquinizarin, 76.0 g (0.200 eq. primary amine) of the amine of Example 2, 30 ml of water, and 0.14 g of boric acid was heated to 100° C under an inert atmosphere. A slurry of 14.40 g (0.0600 moles) of quinizarin in 40 ml of water was added. The reaction mixture was maintained at 100° C. for 25 hours and then cooled to 80° C. A slow stream of air was blown onto the solution for 2 hours. The resulting blue material was stripped under high vacuum to give 91.5 g of the substituted 1,4-dialkylamino anthraquinone colorant (specific absorptivity = 13.6 @$\lambda$ max 636 nm in methanol). The infrared spectrum of this material indicated that hydrolysis of the ketal functionality had essentially not occurred during the reaction.

EXAMPLE 10

The product of Example 9 was hydrolyzed by the following procedure. A solution of 50.0 g of the blue colorant from Example 9 in 50 ml of 50% acetic acid was heated to reflux for 2 hours under a slow argon sparge. The reaction was then stripped under high vacuum to give 46 g of the corresponding hydrolyzed anthraquinone colorant. The presence of the deprotected hydroxyl functionalities were verified by IR, NMR, and hydroxyl number.

EXAMPLE 11

A stirred mixture of 49.5 g (0.100 moles) of the amine of Example 8, 13 g of anhydrous sodium carbonate, 20.0 g of 4-chloro-3-nitrobenzotrifluoride (0.089 moles), and 65 ml of water was heated to gentle reflux for 3 hours. The lower aqueous layer was removed and the remaining crude product was purified by washing with hot water (2×75 ml). After stripping under reduced pressure 54.4 g of yellow colorant were obtained ($\epsilon$=5959,$\lambda_{max}$=412 nm in methanol).

EXAMPLE 12

The product of Example 11 was hydrolyzed by the following procedure. A solution of 25.0 g of the colorant of Example 11 was heated to reflux in 50 ml of 60% acetic acid for 2 hours. After stripping under vacuum there were obtained 23.6 g of the hydrolyzed yellow colorant ($\epsilon$=5820, $\lambda_{max}$=412 nm in methanol).

EXAMPLE 13

This example demonstrates the utility of amino polyoxyalkylene derived colorants for coloration of polyurethanes. Polyurethane foams were prepared with the colorants from examples 9-12 using the following formulation:

| | |
|---|---|
| 100 g | Niax 16-56 (Union Carbide Corp.) |
| 1.0 ml | Silicone L-520 (Union Carbide Corp.) |
| 0.15 ml | Dabco 33LV Amine (Air Products) |
| 49.5 ml | Toluene diisocyanate (B.A.S.F.) |
| 4.5 g | Water |
| 1.0 g | Colorant |

Small samples of each foam were extracted with isopropyl alcohol to determine if the colorant had copolymerized into the urethane polymer. The colorants from examples 9 and 11 were almost completely extractable, whereas the corresponding hydrolyzed products from examples 10 and 12 were virtually nonextractible.

We claim:

1. A polymeric colorant of the formula:

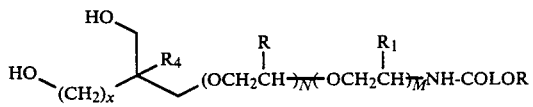

wherein R and $R_1$ are independently selected from hydrogen or lower alkyl; $R_4$ is selected from hydrogen or lower alkyl; x is o or 1; N and M are each integers of from 1 to about 100 and the sum of N and M is from 3 to about 100; and the designation "COLOR" represents a chromophoric molecule.

2. A polymeric colorant according to claim 1 wherein said chromophoric molecule is selected from nitroaryls, methines, azos, disazos, anthraquinones, phrazolones and pyridones.

3. A polymeric colorant according to claim 1 wherein the sum or N and M is from 4 to about 100.

* * * * *